United States Patent [19]
Powell et al.

[11] Patent Number: 5,854,303
[45] Date of Patent: Dec. 29, 1998

[54] POLYMER, ARTICLE AND METHOD FOR INHIBITING THE GROWTH OF OCULAR PATHOGENS IN EYE CARE PRODUCTS

[75] Inventors: Charles Hayes Powell, Irvine; David C. Rupp, San Pedro, both of Calif.

[73] Assignee: Allergan Sales, Inc., Irvine, Calif.

[21] Appl. No.: 13,725

[22] Filed: Jan. 27, 1998

Related U.S. Application Data

[62] Division of Ser. No. 440,579, May 15, 1995, Pat. No. 5,739,178.

[51] Int. Cl.$^6$ ............ C98L 33/14; C98L 33/13; A61K 31/22; C08F 20/10; C07D 303/08; C07D 303/36

[52] U.S. Cl. ............ 523/106; 523/122; 424/427; 424/429; 526/292.2; 526/312; 549/552

[58] Field of Search ............ 523/106, 122; 424/427, 429; 526/292.2, 312; 549/552

[56] References Cited

U.S. PATENT DOCUMENTS

| | | |
|---|---|---|
| 4,499,077 | 2/1985 | Stockel et al. |
| 4,551,461 | 11/1985 | Sherman . |
| 4,654,208 | 3/1987 | Stockel et al. |
| 5,124,359 | 6/1992 | Wachman et al. |
| 5,382,599 | 1/1995 | Rupp et al. |
| 5,486,357 | 1/1996 | Narayanan ............ 424/78.17 |
| 5,739,178 | 4/1998 | Powell et al. ............ 523/122 |

FOREIGN PATENT DOCUMENTS

| | | |
|---|---|---|
| 6756794 | 2/1995 | Australia . |
| 0635733 | 1/1995 | European Pat. Off. . |
| 2025573 | 2/1971 | Germany . |
| 2232187 | 1/1973 | Germany . |

OTHER PUBLICATIONS

Caplus AN 1994:327970 (Jun. 27, 1994).
Caplus AN 1994: 273009 (May 30, 1994).
Gottschalk, G., *Bacterial Metabolism* pp. 1–11 (Springer–VerlagNew York, Inc., 1979).
Ma, P., et al., "Naegleria and AcanthamorebaInfections:Review", *Reviews of Infectious Diseases*, vol. 12, No. 3, pp. 490–513(University of Chicago 1990).
Neff, R.J., "Induction of Synchronous Encystment(Differentiation)in Acanthamoeba sp" *Methods in Cell Physiology*, Ch. 4, pp. 55–83 (D.M.Prescott(Ed), 1977).
Griffin, D., *Fungal Physiology*(John Wiley & Sons, Inc. 1981), pp. 131–167.
Caplus AN 1994:327970(Jun. 27, 1994).
Caplus AN 1994:273009(May 30, 1994).

*Primary Examiner*—Jeffrey Smith
*Assistant Examiner*—Wu C. Cheng
*Attorney, Agent, or Firm*—Carlos A. Fisher

[57] ABSTRACT

A polymeric material incorporating a polyvalent cation chelating agent in an amount effective to inhibit the growth of an ocular pathogen, particularly a protozoan, can be used to produce eye care products such as contact lens cases and containers for containing eye care solutions and contact lenses.

16 Claims, No Drawings

POLYMER, ARTICLE AND METHOD FOR INHIBITING THE GROWTH OF OCULAR PATHOGENS IN EYE CARE PRODUCTS

This is a divisional of U.S. patent application Ser. No. 08/440,579, filed May 15, 1995, now U.S. Pat. No. 5,739,178, incorporated by reference herein.

FIELD OF THE INVENTION

The present invention relates to the inhibition of the growth of ocular pathogens, particularly protozoa, in eye care products such as ophthalmic solutions and on the surfaces of eye care products such as contact lenses. More specifically, the present invention relates to a polymer useful in inhibiting the growth of protozoa and other ocular pathogens, an article comprising the polymer, and a method employing such an article.

BACKGROUND OF THE INVENTION

Eye care products, such as contact lens care systems, are susceptible to contamination by ocular pathogens. Known ocular pathogens include bacteria, fungi, and also protozoans such as amoebae, for example the acanthamoebae. Acanthamoebae are ubiquitous free-living protozoans, which exist in two distinct morphological forms: the trophozoite and the cyst. The trophozoite form is the free swimming form and is relatively easy to kill. The organism encysts in an adverse environment, creating a thick protective coat making it very difficult to kill. The cyst form is the hibernating form of the organism. The organism reverts to the trophozoite form in a favorable environment.

A variety of species of Acanthamoeba have been found to cause infectious keratitis. These species include *A. polyphaga, A. castellanii, A. lenticulata, A. hatchetti, A. astronyxis, A. culbertsoni, A. rhysodes,* and others. See, for example, Ma et al., Rev. Infectious Diseases 1990 May/June; 12(3):490–513 and the references cited therein. Moreover, acanthamoebae use bacteria and fungi as a food source. Co-contamination of contact lens care system with bacteria and fungi facilitates the growth of the acanthamoebae in the contact lens care system, and is thus implicated as a risk factor for acanthamoebic keratitis. The incidence of ulcerative keratitis among soft contact lens wearers in the United States has been found to be a function of contact lens wear mode. An incidence of infection of 4.1 per 10,000 daily wear patients per year and 20.9 per 10,000 extended wear patients per year has been found. Thus of the approximately 20 million contact lens wearers in the United States, over 12,000 infections (from all causes) occur yearly. Acanthamoebic keratitis has been reported in contact lens wearers regardless of lens type.

Various agents have been found to be effective in killing and/or inhibiting the growth of bacteria or fungi. For example, U.S. Pat. No. 4,499,077 to Stockel discloses an antimicrobial composition for soft contact lenses including an oxidizing agent such as an oxyhalogen compound, e.g., stabilized chlorine dioxide or hydrogen peroxide, and a polymeric germicide, e.g., a quaternary ammonium polymer or an amino and/or imino polymer or salts thereof. U.S. Pat. No. 4,654,208 to Stockel discloses an antimicrobial composition for contact lenses including an aqueous solution of a germicidal polymeric nitrogen compound and an oxidizing agent, e.g., chlorine dioxide, chlorite, stabilized chlorine dioxide or hydrogen peroxide, to potentiate the activity of the germicidal polymeric nitrogen compound at low concentrations. However, no agents have been proposed as effective in inhibiting the growth of protozoans.

In U.S. Pat. No. 5,382,599, to Rupp et al., it is disclosed that various polyvalent cation chelating agents, such as EDTA, are effective per se in inhibiting the growth of protozoans, including amoebae such as acanthamoebae. An effective protozoan-growth inhibiting amount of a chelating agent is added directly to an eye care product such as a contact lens care solution.

It would be desirable to provide additional methods and compositions for inhibit the growth of protozoans such as acanthamoebae in or on eye care products such as contact lenses, contact lens solutions and contact lens cases, in order to reduce the incidence of acanthamoebic keratitis and other ophthalmic pathologies due to the presence of protozoans.

It would also be desirable to provide methods and compositions that are effective in inhibiting the growth of other ocular pathogens, such as bacteria or fungi, as well as protozoans.

SUMMARY OF THE PREFERRED EMBODIMENTS

In accordance with one aspect of the present invention, a polyvalent cation chelating polymer capable of inhibiting the growth of ocular pathogens, in particular protozoa, is provided. The polymer has incorporated therein an effective growth inhibiting amount, preferably about 1 to 100 wt %, of a monomer unit containing at least one moiety capable of chelating a polyvalent cation. Very preferably the moiety capable of chelating a polyvalent cation is an $-N(CH_2CO_2A)_2$ group or an $-N(CH_2CO_2A)_3Cl$ group, wherein A is hydrogen or an alkali metal cation.

In a more specific embodiment, the inventive polymer comprises a plurality of monomer units having the formula (I)

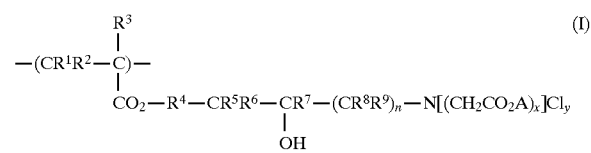

wherein $R^1$, $R^2$, $R^3$ independently are H or a $C_{1-6}$ alkyl group, $R^4$ is a single bond or a $C_{1-6}$ alkylene oxy group, $R^5$, $R^6$, $R^7$, $R^8$, $R^9$ independently are H or a $C_{1-6}$ alkyl group, n is an integer from 0 to 18, A is H or an alkali metal cation, x is 2 or 3, and y is 0 when x is 2 and 1 when x is 3.

The polymer can include one or more comonomeric units obtained from ethylenically unsaturated comonomers, in particular hydrophilic comonomers such as alkyl or hydroxyalkyl (alk)acrylates. Preferred comonomeric units have the formula (II)

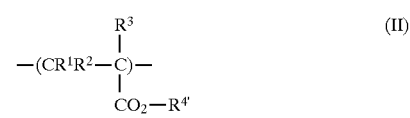

wherein $R^1$, $R^2$, $R^3$ independently are H or a $C_{1-6}$ alkyl group, $R^{4'}$ is H or a $C_{1-6}$ hydroxyalkyl group.

In accordance with another aspect of the present invention, there is provided an eye care product, such as a lens case, a container for an ophthalmic solution, or a contact lens, which comprises a polymer as described above.

In accordance with a further aspect of the present invention, a compound is provided having the formula (III)

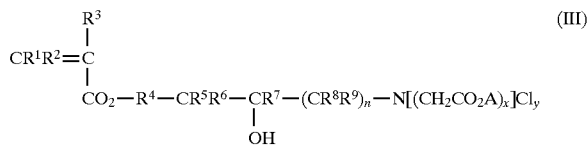

wherein $R^1$, $R^2$, $R^3$ independently are H or a $C_{1-6}$ alkyl group, $R^4$ is a single bond or a $C_{1-6}$ alkylene oxy group, $R^5$, $R^6$, $R^7$, $R^8$, $R^9$ independently are H or a $C_{1-6}$ alkyl group, n is an integer from 0 to 18, A is H or an alkali metal cation x is 2 or 3, and y is 0 when x is 2 and 1 when x is 3.

The compound is particularly suitable for polymerization to produce a polymer capable of chelating a polyvalent cation.

In accordance with yet another aspect of the present invention, methods of producing a composition of matter capable of chelating a polyvalent cation are provided. One more specific embodiment-provides a method which comprises the step of reacting a compound of the formula (IV)

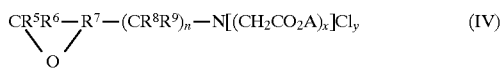

wherein $R^5$, $R^6$, $R^7$, $R^8{}_1$, $R^9$ independently are H or a $C_{1-6}$ alkyl group, n is an integer from 0 to 18, A is H or an alkali metal cation, x is 2 or 3, and y is 0 when x is 2 and 1 when x is 3, with a composition of matter capable of reacting with an epoxide.

One particularly preferred method employs as the composition of matter capable of reacting with an epoxide a plasma treated solid polymer having surface free radicals. This preferred method comprises the steps of exposing the solid polymer to a solution or a low pressure vapor comprising the compound having formula (IV) to form a derivatized solid polymer, and neutralizing residual surface free radicals on the derivatized solid polymer by exposing the solid polymer to liquid water or water vapor at low pressure.

Another particularly preferred method employs as the composition of matter capable of reacting with an epoxide a compound of the formula (V)

wherein $R^1$, $R^2$, $R^3$ independently are H or a $C_{1-6}$ alkyl group, and $R^{4'}$ is H or a $C_{1-6}$ hydroxyalkyl group.

It is particularly preferred to react the compound of formula (IV) with the compound of formula (V) to form a compound of formula (III) as described above.

Another more specific embodiment of a method of producing a composition of matter capable of chelating a polyvalent cation comprises the step of polymerizing a compound of formula (III) as described above. Optionally, the compound of formula (III) can be copolymerized with one or more additional ethylenically unsaturated monomers.

Compositions of matter produced according to the foregoing methods, and eye care products comprising the inventive polymers and compositions of matter, are also provided, as are methods of inhibiting the growth of ocular pathogens, particularly protozoa, using the inventive eye care products.

Other objects, features and advantages of the present invention will become apparent to those skilled in the art from the following detailed description. It is to be understood, however, that the detailed description and specific examples, while indicating preferred embodiments of the present invention, are given by way of illustration and not limitation. Many changes and modifications within the scope of the present invention may be made without departing from the spirit thereof, and the invention includes all such modifications.

DETAILED DESCRIPTION OF THE PREFERRED EMBODIMENTS

U.S. Pat. No. 5,382,599, to Rupp et al., the disclosure of which is incorporated in its entirety herein by reference, describes methods and compositions for inhibiting the growth of protozoa in or on the surface of an eye care product. According to Rupp et al., the growth of protozoa is inhibited by contacting the eye care product with an effective protozoan growth-inhibiting amount of a polyvalent cation chelating agent, such as EDTA. The polyvalent cation chelating agent is typically added to an eye care solution to inhibit protozoan growth therein, or to inhibit protozoan growth on the surface of an eye care product with which the solution is in contact.

It has now been discovered that polymers and related compositions of matter can be produced which include a plurality of moieties which are capable of chelating polyvalent cations. The inventive materials thus are also capable of inhibiting the growth of protozoa.

As used herein, a "polyvalent cation chelating polymer" is a polymer which includes at least one moiety that is capable of forming coordination bonds with a cation having a positive charge of at least 2. Such cations include, for example, $Ca^{2+}$, $Mg^{2+}$, $Fe^{2+}$, $Fe^{3+}$, $Mn^{2+}$, $Zn^{2+}$, $Cu^{2+}$ and $Ni^{2+}$ including combinations of two or more such moieties are also included within the scope of this term.

In protozoan cells, particularly acanthamoeba cells, polyvalent cations such as calcium, magnesium, iron, manganese, and zinc serve as cofactors of enzymes required for metabolism. These polyvalent cations also affect the function and structure of the trophozoite by influencing the tonicity of the environment. Calcium and magnesium have been shown in the literature to be essential for acanthamoeba encystment. See Neff et al., "Induction of Synchronous Encystment (Differentiation) in Acanthamoeba sp.," Methods in Cell Physiology, vol. 1, ch. 4, pp. 55–83 (D. M. Prescott, ed., Academic Press, New York 1977). Calcium salts have also been shown to affect acanthamoeba ameboid locomotion and attachment.

Applicants have thus found that the use of polymers that include polyvalent cation chelating moieties effectively inhibits protozoan cell functions, particularly cell growth, which require such cations.

As used herein, a polyvalent cation chelating polymer "effectively inhibits" protozoan growth if exposure of a solution including a known initial number of protozoa to the polymer over a period of at least seven days results in a constant or reduced number of protozoa. Inhibition of protozoan growth includes in particular prevention of excystment of the protozoa.

The invention is effective in inhibiting the growth of protozoans including, but not limited to, acanthamoebae, for example *A. polyphaga, A. castellani, A. lenticulata, A. hatchetti, A. astronyxis, A. culbertsoni,* and *A. rhysodes.* The invention is also effective in inhibiting the growth of other protozoans, such as amoebae of the genus Naegleria.

Many other ocular pathogens besides protozoa require one or more of the foregoing polyvalent cations for growth. See, e.g., Griffin, D., *Fungal Physiology* (John Wiley & Sons, Inc. 1981), p. 138 (essential mineral nutrients of fungi); Gottschalk, G., *Bacterial Metabolism* (Springer-Verlag New York, Inc. 1979, 1986) pp. 1–3 (minerals essential for bacterial nutrition). Thus, the inventive compositions of matter can inhibit the growth of harmful bacteria and fungi as well as protozoans. Exemplary ocular pathogens whose growth can be inhibited by recourse to the present invention include *P. aeruginosa, C. albicans* and *S. marcescens*.

The present invention provides compositions of matter that can be used in the manufacture of contact lenses, contact lens cases, ophthalmic and lens treatment solution containers, and other products.

The compositions of matter capable of chelating a polyvalent cation according to the instant invention may broadly be characterized as solid or hydrogel polymeric materials. The inventive polymeric materials can be prepared in a number of ways. A monomer including a polyvalent cation chelating moiety can be synthesized and subsequently polymerized, optionally together with one or more comonomers, to produce a polymer incorporating the chelating moiety. Alternatively, a polymeric material not including a polyvalent cation chelating moiety can be chemically modified to incorporate such moieties at least on its surface. For example, an article comprised of a polymeric material can be exposed to a plasma discharge which results in the formation of free radicals on the surface of the material. The treated surface can them be contacted with an agent including a chelating moiety to produce a derivatized surface capable of chelating polyvalent cations.

In one preferred embodiment, a polymer is provided which comprises an effective growth inhibiting amount, preferably a protozoan growth inhibiting amount, of at least one moiety capable of chelating a polyvalent cation. Preferably, the polymer includes about 1 to 100 wt %, based on the weight of the polymer, of one or monomer units which comprise the moiety or moieties. Particularly preferred moieties are the —N(CH$_2$CO$_2$A)$_2$ group and the —N(CH$_2$CO$_2$A)$_3$Cl group, wherein A is hydrogen or an alkali metal cation.

A particularly preferred embodiment of a polymer capable of chelating polyvalent cations comprises a plurality of monomer units having the formula (I)

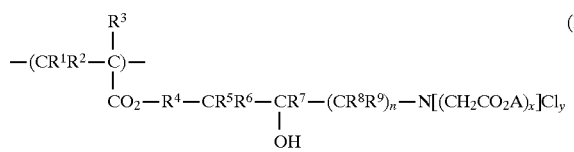

wherein
$R^1$, $R^2$, $R^3$ independently are H or a $C_{1-6}$ alkyl group,
$R^4$ is a single bond or a $C_{1-6}$ alkylene oxy group,
$R^5$, $R^6$,
$R^7$, $R^8$, $R^9$ independently are H or a $C_{1-6}$ alkyl group,
n is an integer from 0 to 18,
A is H or an alkali metal cation,
x is 2 or 3, and
y is 0 when x is 2 and 1 when x is 3.

In preferred embodiments of the polymer of formula (I), $R^1$ and $R^2$ are H. $R^3$ preferably is CH$_3$. $R^5$, $R^6$, $R^7$, $R^8$ and $R^9$ preferably are H. $R^4$ preferably is a single bond or an ethylene oxy group. A preferably is H or Na. Preferably, n is 12.

Preferred polymers include about 500 to 10,000 monomer units of formula (I).

In another preferred embodiment, the inventive polymer includes at least one comonomer unit, for example, hydrophilic comonomers such as alkyl or hydroxyalkyl (alk) acrylates. Polymers for use according to the invention in producing contact lenses can includes as comonomers such "hydrogel" monomers as hydroxyethyl methacrylate, hydroxyethyl methyl methacrylate, vinylpyrrolidone, glyceromethacrylate, methacrylate esters and the like. Other comonomers, such as propylene, vinyl chloride, vinylidene chloride, vinyl acetate, etc., can be employed to produce polyvalent cation chelating polymers for use in producing other types of products, such as contact lens cases. Alternatively, lens cases and lens case components constructed of a hard polymer, such as polyethylene, polystyrene, polycarbonate, polyvinyl chloride or other conventional polymers, can be coated with a hydrogel polymer as described herein, i.e., a polymer including about 1 to 100 wt % of a monomeric unit or units that include a polyvalent cation chelating moiety.

Specific preferred comonomeric units have the formula (II)

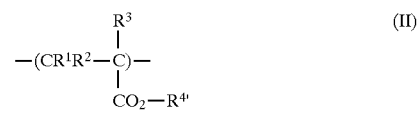

wherein
$R^1$, $R^2$, $R^3$ independently are H or a $C_{1-6}$ alkyl group,
$R^{4'}$ is H or a $C_{1-6}$ hydroxyalkyl group.

A contact lens including a polymer according to the instant invention can comprise a laminated structure in which a layer comprised of the inventive polymer is sandwiched between conventional hydrogel layers. Alternatively, a two-layer structure can include an outer layer comprised of the inventive polymer and an inner layer (i.e., the layer in contact with the eye) of a conventional hydrogel-type polymer. Such a structure can increase the useful lifespan of the contact lens by inhibiting microbial penetration into and proliferation within the lens matrix, thus inhibiting damage to the lens.

The present invention further provides compounds which can be polymerized to produce a polyvalent cation chelating polymer. Compounds of the formula (III)

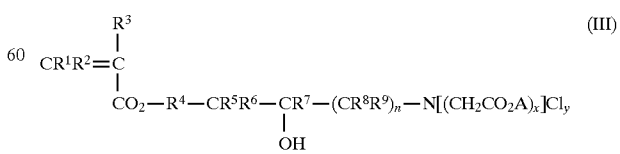

wherein
$R^1$, $R^2$, $R^3$ independently are H or a $C_{1-6}$ alkyl group,
$R^4$ is a single bond or a $C_{1-6}$ alkylene oxy group, $R^5$, $R^6$, $R^7$, $R^8$, $R^9$ independently are H or a $C_{1-6}$ alkyl group, n is an integer from 0 to 18, A is H or an alkali metal cation x is 2 or 3, and y is 0 when x is 2 and 1 when x is 3, can be polymerized, either alone or with one or more comonomers, to produce polymers as described herein.

In particular preferred embodiments, $R^1$ and $R^2$ are H. $R^3$ can preferably be $CH_3$. $R^5$, $R^6$, $R^7$, $R^8$ and $R^9$ can preferably be H. Preferably, $R^{4'}$ is a single bond or an ethylene oxy group. A preferably is H or Na, and n preferably is 12.

Polymerization of compound (III) preferably is carried out using a solvent such as glycerol, other glycols, acetic acid, $C_{1-6}$ alcohols, water, and combinations thereof.

The instant invention also provides methods for producing compositions of matter which are capable of chelating polyvalent cations. The inventive methods generally include the step of reacting a compound of the formula (IV)

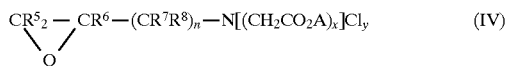

wherein $R^5$, $R^6$, $R^7$, $R^8$ independently are H or a $C_{1-6}$ alkyl group, n is an integer from 0 to 18, A is H or an alkali metal cation, x is 2 or 3, and y is 0 when x is 2 and 1 when x is 3, with a composition of matter capable of reacting with an epoxide.

According to a first preferred embodiment of a method of the invention, the composition of matter capable of reacting with an epoxide is a plasma treated solid polymer having surface free radicals. In this embodiment, an article comprised of a solid polymer, such as polycarbonate, polypropylene, polyvinyl acetate or polyvinyl chloride, is exposed to a plasma at low pressure (about 0.01 to 1 mm Hg) or in an inert gas atmosphere ($N_2$, Ne, Xe, etc.), which results in the formation of free radicals on the treated surface as is well known to those skilled in the art. Next, the treated surface is exposed to a solution or a low pressure (about 0.01–1 mm Hg) vapor comprising a compound of formula (IV). This results in the formation of a derivatized solid polymer having polyvalent cation chelating groups bonded to the polymer surface. Next, the derivatized solid polymer is exposed to liquid water or water vapor at low pressure (about 0.1–10 mm Hg) in order to neutralize any residual surface free radicals on the derivatized solid polymer and stabilize the derivatized solid polymer.

In another embodiment of the inventive method, a hydrophilic ("soft") contact lens comprised of a conventional hydrogel polymer is manufactured according to any conventional method. Lenses comprised of or containing hydroxyethyl methacrylate or methacrylic acid are particularly suitable. After manufacture, but prior to extraction or hydration of the lens, the lens is contacted with a compound of formula (IV) in a liquid carrier or in neat form, preferably in the presence of a catalyst such as pyridine or triethylamine. After the esterification reaction is complete, the contact lens is soaked, preferably in an aqueous solution, to remove unreacted starting materials and side products. The lens is then dried. The matrix of the derivatized contact lens now includes polyvalent cation chelating moieties.

According to another embodiment of the foregoing method, a compound having the formula (V)

wherein $R^1$, $R^2$, $R^3$ independently are H or a $C_{1-6}$ alkyl group, and $R^{4'}$ is H or a $C_{1-6}$ hydroxyalkyl group, and is reacted with a compound of formula (IV), preferably in the presence of an organic base such as pyridine or triethylamine, to afford compound (III), described above, which is capable of chelating a polyvalent cation and which can be polymerized to produce a polyvalent cation chelating polymer.

Compositions of matter according to this aspect of the invention can be used in many applications. For example, the polymers can be used in the manufacture of hydrogel contact lenses. The polymers can also be used to produce or form a surface coating on components of lens cases or containers used for storing ophthalmic and contact lens care solutions or contact lenses. In the alternative, the foregoing articles of manufacture can be produced using conventional polymers. Subsequently at least a portion of the surface area of such articles can then be modified as described herein, such as by plasma treatment followed by reaction with compounds of formula (IV), or by application of a coating including a polymer as described herein.

According to a preferred embodiment, the growth of ocular pathogens, in particular protozoan growth, on the surfaces of eye care products such as contact lenses can also be inhibited by using the present invention. For example, the contact lens can be placed in contact with a solution contained in the contact lens cases and containers made of the polymers incorporating the polyvalent cation chelating agent.

The invention is further illustrated by the following non-limiting examples:

EXAMPLE 1

Polymer having incorporated therein a polyvalent cation chelating agent 130 g (1 mol) of hydroxyethyl methacrylate is reacted with 343 g (1 mol) of 1,2-epoxy-myristylamine diacetic acid (formula IV, $R^{5-9}$=H, A=H, n=12, x=2, y =0) in the presence of 130 mg of pyridine. The reaction is carried out for 50 minutes at 80° C. to afford compound (1):

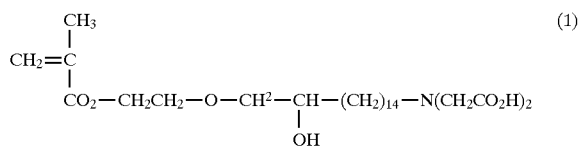

100 g of compound (1) are then dissolved in 50 g of ethylene glycol solvent together with 500 mg of benzoyl peroxide as a polymerization initiator. The reaction mixture is exposed to ultraviolet light, and the polymerization reaction is carried out for 100 minutes at a temperature of 40° C. to afford a polymer having about 100 wt % of monomeric units which include a polyvalent cation chelating moiety (—$N(CH_2CO_2H)_2$).

EXAMPLE 2

Polymer having incorporated therein a polyvalent cation chelating agent 100 g of compound (1) and 100 g of hydroxyethyl methacrylate are dissolved in 100 g of ethylene glycol solvent together with 500 mg of benzoyl peroxide as a polymerization initiator. The reaction mixture is exposed to ultraviolet light, and the polymerization reaction is carried out for 100 minutes at a temperature of 40° C. to afford a polymer having about 50 wt % of monomeric units which include a polyvalent cation chelating moiety.

What is claimed is:

1. An eye care product comprising a polymer comprising a plurality of monomers of the formula:

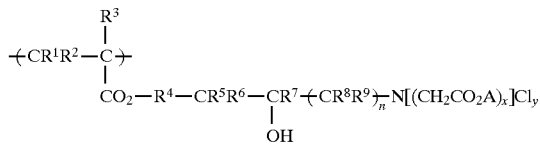

wherein:

$R^1$, $R^2$, $R^3$, $R^5$, $R^6$, $R^7$, $R^8$ and $R^9$ are, independently, selected from the group consisting of H or a $C_{1-6}$ alkyl group, and;

$R^4$ is selected from the group consisting of a single bond or a $C_{1-6}$ alkenyl oxy group, and;

n is an integer from 0 to 18, and;

A is selected from the group consisting of H or an alkali metal cation, and x consists of 3, and;

y consists of 1.

2. The eye care product of claim 1 comprising a contact lens.

3. The eye care product of claim 1 comprising a contact lens case.

4. The eye care product of claim 1 comprising a container for an ophthalmic or contact lens care solution.

5. A contact lens comprising:

a polymer comprising a plurality of monomers of the formula:

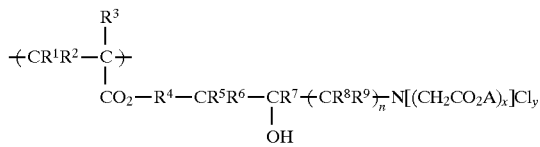

wherein i) $R^1$, $R^2$, $R^3$, $R^5$, $R^6$, $R^7$, $R^8$ and $R^9$ are independently selected from the group consisting of H or a $C_{1-6}$ alkyl group;

ii) $R^4$ is selected from the group consisting of a single bond or a $C_{1-6}$ alkenyl oxy group;

iii) n is an integer from 0 to 18;

iv) A is selected from the group consisting of H or an alkali metal cation;

v) x consists of 3; and vi) y consists of 1.

6. The contact lens of claim 4 wherein said polymer is disposed on a surface of said contact lens.

7. The contact lens of claim 4 further comprising:

at least one ethylenically unsaturated comonomer unit consisting of the formula:

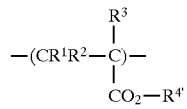

wherein i) $R^1$, $R^2$, and $R^3$ are independently selected from the group consisting of H or a $C_{1-6}$ alkyl group, and ii) $R^{4'}$ is selected from the group consisting of H or a $C_{1-6}$ hydroxyalkyl group.

8. The contact lens of claim 6 wherein said polymer is disposed on a surface of said contact lens.

9. A container comprising a composition capable of chelating a polyvalent cation, said composition made by a method comprising the step:

reacting a compound of the formula:

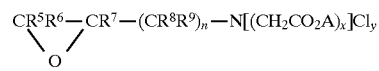

wherein i) $R^5$, $R^6$, $R^7$, $R^8$, and $R^9$ are independently selected from the group consisting of H or a $C_{1-6}$ alkyl group;

ii) n is an integer selected from the group consisting of 1–18;

iii) A is selected from the group consisting of H or an alkali metal cation;

iv) x is selected from the group consisting of 2 and 3; and v) y is selected from the group consisting of 0 when x is 2 and 1 when x is 3;

with a composition capable of reacting with an epoxide.

10. The container of claim 8 comprising a contact lens case.

11. The container of claim 8 comprising a container for an ophthalmic or contact lens care solution.

12. The container of claim 8 wherein said composition capable of reacting with an epoxide comprises a plasma-treated polymer comprising surface free radicals.

13. The container of claim 11 comprising a contact lens case.

14. The container of claim 11 comprising a container for an ophthalmic or contact lens care solution.

15. A contact lens comprising a composition capable of chelating a polyvalent cation, said composition made by a method comprising the step:

reacting a compound of the formula:

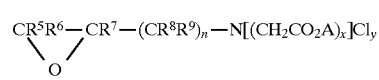

wherein i) $R^5$, $R^6$, $R^7$, $R^8$, and $R^9$ are independently selected from the group consisting of H or a $C_{1-6}$ alkyl group;

ii) n is an integer selected from the group consisting of 1–18;

iii) A is selected from the group consisting of H or an alkali metal cation;

iv) x is selected from the group consisting of 2 and 3; and v) y is selected from the group consisting of 0 when x is 2 and 1 when x is 3;

with a composition capable of reacting with an epoxide.

16. The contact lens of claim 14, wherein said composition capable of reacting with an epoxide comprises a plasma-treated polymer comprising surface free radicals.

* * * * *